United States Patent [19]
Cahn et al.

[11] 3,993,457
[45] Nov. 23, 1976

[54] CONCURRENT PRODUCTION OF METHANOL AND SYNTHETIC NATURAL GAS

[75] Inventors: Robert P. Cahn, Milburn; John P. Longwell; Stephen L. Wythe, both of Westfield, all of N.J.

[73] Assignee: Exxon Research and Engineering Company, Linden, N.J.

[22] Filed: Nov. 26, 1975

[21] Appl. No.: 635,367

Related U.S. Application Data

[63] Continuation-in-part of Ser. No. 384,061, July 30, 1973, abandoned.

[52] U.S. Cl. ............................... 48/197 R; 48/202; 48/209; 48/210; 48/211; 260/449 M; 260/449.5

[51] Int. Cl.² ............................................ C10K 3/04

[58] Field of Search ............... 48/197 R, 202, 209, 48/210, 211, 212, 213, 214, 215; 252/373; 260/449 R, 449 M, 449.5, 449.6, 450; 423/361, 369

[56] References Cited

UNITED STATES PATENTS

| | | | |
|---|---|---|---|
| 1,824,896 | 9/1931 | Jager | 260/449 R |
| 1,831,179 | 11/1931 | Jager | 260/449.5 |
| 2,094,027 | 9/1937 | Stitzer | 48/65 |
| 2,276,343 | 3/1942 | Reyerson et al. | 48/202 |
| 2,713,590 | 7/1955 | Palmer et al. | 48/206 |
| 2,912,315 | 11/1959 | Haney | 48/214 |
| 3,262,886 | 7/1966 | Bernas et al. | 48/215 |
| 3,424,554 | 1/1969 | Jahnig et al. | 208/50 |
| 3,598,527 | 8/1971 | Quartulli et al. | 423/361 |

*Primary Examiner*—S. Leon Bashore
*Assistant Examiner*—Peter F. Kratz
*Attorney, Agent, or Firm*—J. W. Ditsler

[57] ABSTRACT

Methanol and synthetic natural gas are produced concurrently by introducing a carbonaceous material into a gasification zone, and thereafter, passing sequentially the synthesis gas thus formed through a water gas shift conversion zone, a sulfur compound and carbon dioxide removal zone, a methanol synthesis zone and a methanation zone.

21 Claims, 1 Drawing Figure

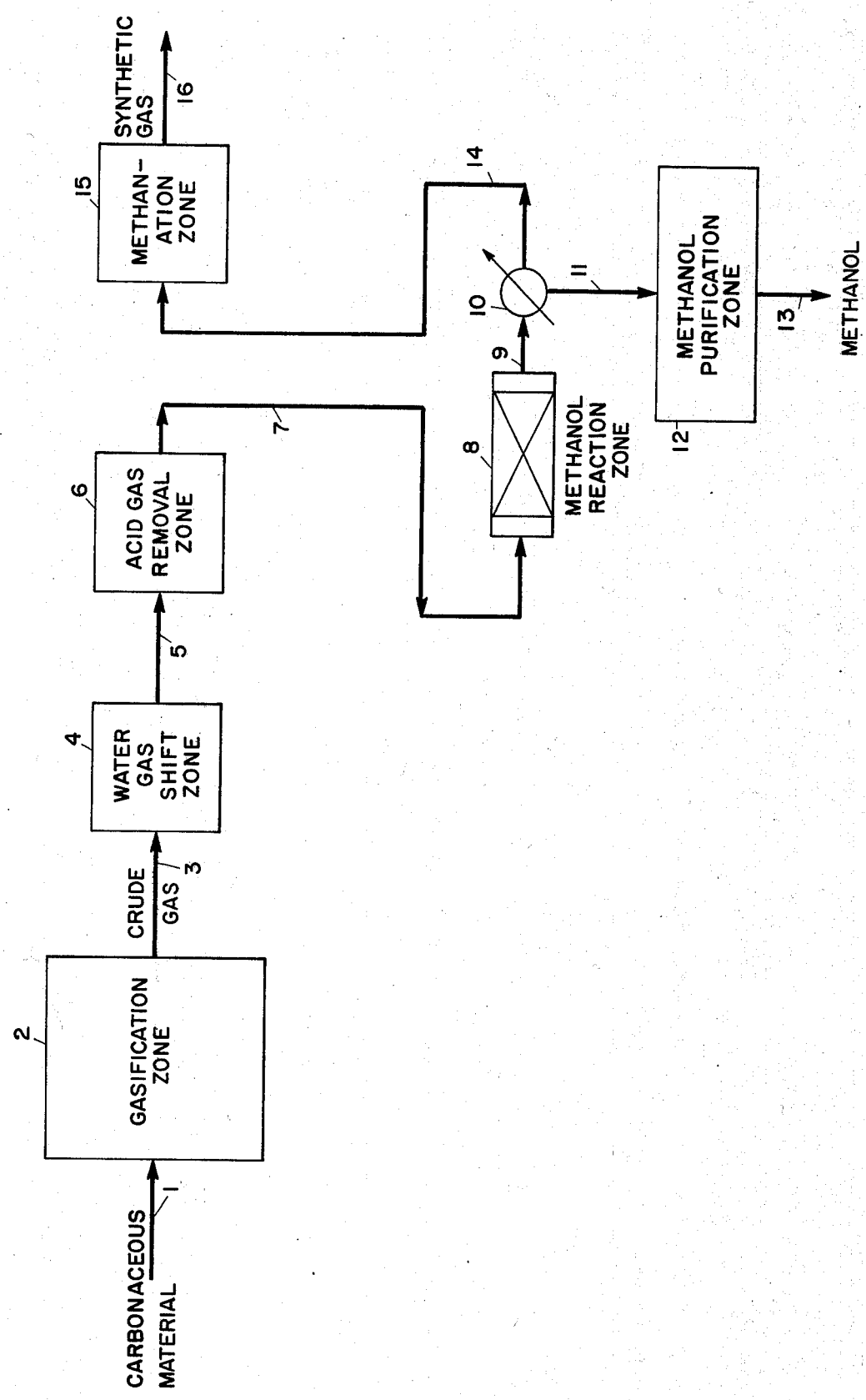

CONCURRENT PRODUCTION OF METHANOL AND SYNTHETIC NATURAL GAS

CROSS-REFERENCE TO RELATED CASES

This is a continuation-in-part of application Ser. No. 384,061, filed July 30, 1973, now abandoned.

BACKGROUND OF THE INVENTION

1. Field of the Invention

The present invention relates to an integrated process for the concurrent production of methanol and synthetic natural gas from a carbonaceous solid or liquid material.

2. Description of the Prior Art

The prior art considered in the preparation of this specification is as follows: U.S. Pat. Nos. 1,735,925; 1,741,307; 1,741,308; 1,824,896; 1,831,179; 2,276,343; 3,598,527; and 3,666,682. All of these publications are to be considered as incorporated, in toto, herein by reference.

The present "energy crisis" is placing an increasing burden upon available fuel sources. Methanol and synthetic natural gas are fuels which can help alleviate this crisis. Synthetic natural gas, which is substantially methane, can be prepared from the gasification of a carbonaceous solid, e.g. coal, or liquid materials such as high boiling petroleum residues. However, such gasification processes are relatively expensive. Normally, methanol is manufactured by the catalytic conversion of a synthesis gas mixture containing carbon oxides and hydrogen at elevated pressure. The synthesis gas mixture is usually prepared by steam reforming a natural gas or a refinery gas stream having a high methane content. However, the synthesis gas mixture thus produced is too rich in hydrogen for the stoichiometry of the methanol synthesis reaction. This can be remedied by adding extraneous carbon dioxide to the methanol synthesis to achieve a suitable hydrogen/carbon oxides balance. Since methanol is manufactured at elevated pressures and carbon dioxide is usually available at lower pressures, it is usually necessary to compress the carbon dioxide, thus requiring an additional expenditure for the compressor.

The synthesis of methanol from natural gas is becoming increasingly unattractive as the availability of natural gas decreases and as the gas supplies are supplemented by synthetic substitutes derived from other fossil fuel sources; i.e., naphtha or heavy carbonaceous materials such as coal, coke, and petroleum residues. A synthesis gas suitable for use in the production of methanol from such heavy carbonaceous materials can be obtained by high temperature partial oxidation using essentially pure oxygen. However, this process is very expensive on the scale required for reasonably sized methanol plants.

In addition, the synthesis of methanol from carbon oxides and hydrogen is an equilibrium reaction which requires extensive recycle of unconverted reactants through a high pressure reactor to achieve the high degree of conversion necessary for an economical operation as well as the complete utilization of the expensive synthesis gas constituents. However, the accumulation of inerts in the recycle stream and an imbalance in the ratio of hydrogen to carbon oxides results in undesirable high purge rates of synthesis gas and requires expensive recycle compressor and reactor requirements. Furthermore, the synthesis of methanol from carbon oxides is highly exothermic but requires less hydrogen and releases less heat of reaction than does the production of an equivalent amount of methane. Since the shift reaction, which forms hydrogen from carbon monoxides and steam, is also strongly exothermic, the net result is that for a given amount of carbon oxide/hydrogen mixture, methanol production for fuel results in more Btu's being available to the consumer than from methane production. Similarly, the conversion of a given amount of synthesis gas mixture ($CO$, $CO_2$ and $H_2$) to methanol releases less waste heat in the process than does the conversion to methane.

Presently, it is considered uneconomical to build and operate low capacity methanol plants using reciprocating compressors for feed compression and recycle gas compression. In addition, as mentioned above, compressors are also frequently required in methanol synthesis because the steam reformed gas does not contain sufficient carbon oxides for the amount of methanol that could be prepared from a given amount of gas feed. Therefore, a methanol synthesis facility is often dependent upon the continued availability of an extraneous source of carbon dioxide, such as from a neighboring ammonia or hydrogen manufacturing facility. Thus, when the operation of a neighboring facility is interrupted such that the supply of carbon dioxide is adversely affected, methanol production may have to be reduced or even discontinued. However, these and other disadvantages commonly associated with the high costs of both synthetic natural gas production and methanol synthesis have now been overcome by the use of the present invention.

SUMMARY OF THE INVENTION

Now according to the present invention, it has been unexpectedly discovered that the above disadvantages can be overcome by use of an integrated process for the concurrent production of methanol and synthetic natural gas from a carbonaceous solid or liquid material. More specifically, this integrated process comprises gasifying a carbonaceous solid or liquid material to form a crude synthesis gas which is then subjected to a water gas shift reaction under controlled conditions to provide the necessary stoichiometry for the subsequent production of methanol and additional quantities of methane. The "shifted" or converted synthesis gas is then passed to a carbon dioxide and sulfur compounds removal zone, followed in series by a methanol synthesis zone and a methanation zone. The desired end products, i.e. methanol and synthetic natural gas, are concurrently and respectively withdrawn from the latter two zones.

BRIEF DESCRIPTION OF THE DRAWING

The single FIGURE is a schematic flowsheet of the process of the present invention and represents a preferred embodiment thereof.

DETAILED DESCRIPTION OF THE INVENTION

Having thus described the invention in general terms above, reference is now made to the FIGURE. Such details are included as are necessary for a clear understanding of the present invention. No intention is made to unduly limit the scope of the present invention to the particular configuration shown as other configurations are contemplated. Various items such as valves, pumps, compressors, steam lines, instrumentation and other process equipment and control means have been omit- ted therefrom for the sake of simplicity. Variations obvious to those having ordinary skill in the art of methanol synthesis and synthetic natural gas production are included within the broad scope of the present invention.

Referring now to the FIGURE, a carbonaceous solid or heavy liquid material is introduced via line 1 into a gasification zone 2 wherein said material is contacted with injected steam. The reaction therebetween results in the production of a crude synthesis gas (at 1000°–2000° F and 50–1500 psig) comprising $H_2$, CO, $CO_2$, $CH_4$, $H_2S$, $H_2O$, which exits via line 3 and is introduced into the water gas shift conversion zone 4. In the shift conversion zone 4, at least a portion of the carbon monoxide contained in said synthesis gas is reacted (at 50–1500 psig and 500°–800° F) with steam to form carbon dioxide and hydrogen. The "shifted" or converted gas is then discharged from shift conversion zone 4 via line 5 and introduced into the acid gas removal zone 6 wherein sulfur compounds, e.g. hydrogen sulfide, and a substantial portion but not necessarily all, of the carbon dioxide are removed therefrom. The substantially purified synthesis gas then exits from acid gas removal zone 6 via line 7 and is introduced into a methanol synthesis zone which comprises a methanol reaction zone containing at least one methanol reactor (400°–700° F and 250–1500 psig) and a methanol purification zone in series. The purified gas is first introduced into methanol reaction zone 8 via line 7 wherein carbon monoxide and hydrogen are converted catalytically to methanol. The molar ratio of carbon monoxide to hydrogen reacted therein is about 1:2. Carbon dioxide will also react with hydrogen to form methanol, but the relative consumptions of carbon dioxide and hydrogen will be in the molar ratio of 1:3. The gases then exit methanol reaction zone 8 via line 9 and pass through a cooler and knock-out device 10 wherein a portion thereof, which is substantially methanol, is recovered. The methanol thus recovered is then passed via line 11 into methanol purification zone 12 and subjected to a purification therein. Only one reaction zone 8 and one purification zone 9 have been shown in the FIGURE to illustrate methanol synthesis and recovery. However, depending upon the process conditions and the degree of methanol conversion desired, the number of such zones may vary from a single zone as shown to as many as 3 or 4 or more in series, with intermediate methanol removal. Thereafter, substantially purified methanol, which can be utilized commercially as such or subjected to further purification steps, is discharged from purification zone 12 via line 13. The remaining synthesis gas which has not undergone methanol synthesis in reaction zone 8 is then introduced via line 14 into the methanation zone 15 wherein the carbon oxides remaining in said synthesis gas are converted catalytically to methane via reaction (at 400°–800° F and 250–1500 psig) with hydrogen. The methane so produced in methanation zone 15 is combined with the methane already present in the synthesis gas and exits therefrom via line 16 as a synthetic natural gas which is substantially methane and which is suitable for direct injection (at pressures of about 1000 psig) into a gas pipeline for commercial use. Appropriate compression facilities, not shown in the attached FIGURE, can be provided anywhere in the process sequence, but preferably after shift conversion zone 4.

The carbonaceous solid or liquid material intoduced into gasification zone 1 may be any material which contains carbon and which will ultimately, when gasified, produce a crude synthesis gas containing methane, carbon monoxide, carbon dioxide, sulfur compounds, hydrogen and water. Suitable carbonaceous materials include bituminous, sub-bituminous, lignite or brown coal as well as other essentially organic sources such as coke, char, solidfied petroleum, residua and the like. Preferred carbonaceous materials are coal and residua. The term residua as used herein includes crude oils, heavy residuum materials such as atmospheric and vacuum residua, crude bottoms, tar, pitch, asphalt, deasphalted residua, bottoms from catalytic cracking process fractionators, coker produced oils, cycle oils, viscous wax fractions, heavy hydrocarbon pitch forming residua and the like. Preferably, at least a portion of the residua boils above about 650° F at atmospheric pressure. Such carbonaceous materials may be derived from petroleum sources as well as from shale oil kerogen, tar sands bitumen, synthetic oils, coal hydrogenation and the like. Other suitable carbonaceous materials include cellulosic materials such as wood, wood chips, sawdust, paper, etc; other agricultural and forestry waste and by-product materials, e.g. corn husks, bagane, bark etc, and municipal wastes such as garbage.

In gasification zone 1, the carbonaceous solid or liquid material is gasified to form a crude synthesis gas containing the aforementioned components. The gasification of the carbonaceous material can be carried out in any convenient manner and in any suitable apparatus as long as the desired product, i.e., a crude synthesis gas, is produced. It is usually desirable to maximize the production of methane within the gasification zone so as to minimize the heat duty therein as well as the amount of shifting, acid gas removal and methanation which have to be carried out subsequently. Present coal gasification processes generate up to about one-half of their total methane product directly in the gasification zone, while the remaining half is produced in the methanation zone. This results in about 5–30 mole %, preferably 10–30 mole %, methane being present in the crude (dry) synthesis gas from the gasification zone. Other gasification processes, especially those based on partial oxidation produce crude synthesis gases containing between 0.5 and about 5.0 mole % methane. It is a typical embodiment herein that the gasification be carried out, particularly utilizing coal as the carbonaceous solid material, in accordance with the processes described and claimed in Ser. No. 509,880, filed Sept. 27, 1974, which is a continuation-in-part of Ser. No. 238,895, filed Mar. 28, 1972, now abandoned. Both applications are assigned to a common assignee, as is the present specification, and are to be considered as incorporated in toto herein by reference.

In application Ser. No. 509,880, there is described a process wherein subdivided carbonaceous feed solids containing volatilizable hydrocarbons, e.g. coal, are hydrogasified by heating the solids to at least minimum hydrogasification temperature while in dilute phase suspension in a gas containing molecular hydrogen and in contact with subdivided hot solids having a temperature greater than minimum hydrogasification temperature. The feed and hot solids are passed co-currently with the hydrogen-containing gas through a transfer line hydrogasification zone having a length which, for the velocity of the solids passage therethrough, limits the residence time of the solids therein to the time that is necessary to devolatilize the carbonaceous feed solids and to convert a predetermined proportion of the carbon of the feed solids to methane. Suitably from about 1 to about 50 mole % of the carbon in the carbonaceous feed solids is converted to methane. Preferably, the hydrogen-containing gas is produced in a fluidized bed steam gasification reaction zone into which carbonaceous solids from the transfer line hydrogasification zone are charged after separation therefrom of product gases containing methane.

In a preferred embodiment, the transfer line hydrogasification reaction zone is coupled with a fluidized bed steam gasification reaction zone for generating the hydrogen-containing gas, and subdivided coal feed solids are suspended with hot char solids withdrawn from the fluidized bed of the steam gasification reaction zone. The solids are transported in dilute phase through the transfer line hydrogasification zone by a hot, hydrogen-containing gas separately withdrawn from the steam gasification reaction zone. The steam gasification reaction zone is operated at a temperature in the range from about 1500° to about 2000° F and at a pressure in the range from about 50 to about 1000 psia. Thus, the char solids and the hydrogen-containing gas withdrawn from the fluidized bed reaction zone will have a temperature in the range from about 1500° to about 2000° F. Because the char solids from the fluidized bed reaction zone have more heat capacity than the hydrogen-containing gas, the feed coal solids transported through the transfer line hydrogasification zone are heated principally by contact with the hot char moving concurrently through the reaction zone. The heated coal undergoes devolatilization and the carbon in the coal reacts rapidly with hydrogen in the hydrogen-containing gas to produce methane. The gas thus produced (crude synthesis gas) is recovered from the transfer line hydrogasification zone and sent to the water shift conversion zone (hereinafter described). The residual coal solids and the char solids recovered from the gas are recycled to the fluidized bed steam gasification zone.

The solids in the steam gasification reaction zone are maintained in a dense, turbulent fluidized bed by an upwardly flowing stream of saturated or superheated steam, alone or in combination with other gaseous material, so as to resemble and to have the hydrostatic and hydrodynamic characteristics of a boiling liquid. The use of a fluidized bed is particularly advantageous, especially in continuous operations, because it provides for larger solid reaction surfaces, better mixing, greatly improved temperature control and generally higher yields of hydrogen than can be obtained in fixed or gravitating bed operations. Furthermore, the use of a fluidized bed facilitates the handling of solids, permitting them to be treated in a manner analogous to that used for liquids and thus simplifying their withdrawal and transfer into the transfer line hydrogasification reaction zone.

The heat required to maintain the desired operating temperatures within the fluidized bed steam gasification reaction zone reactor may be supplied in any of several different ways. For example, sufficient quantities of an oxidizing gas may be supplied to the steam gasification reaction zone to generate by partial combustion within that zone the heat required by the steam gasification reaction to produce the hydrogen-containing gas. Preferably, however, the necessary heat is supplied as sensible heat by burning solid carbonaceous gasification residues with air in a separate combustion zone and circulating highly heated combustion residues from this combustion zone to the steam gasification reaction zone. The latter method has the advantage of avoiding dilution of the product gases with inert gas.

An example of another gasification process suitable for use in the present invention is described in U.S. Pat. No. 3,838,994, the disclosures of which are incorporated herein by reference. In this process, heavy hydrocarbon feeds are converted to a methane rich vaporous product by contacting said feeds with steam in a reaction zone containing a particulate catalyst bed comprising an alkali metal component, a solid particulate support and an in situ formed carbonaceous deposit on said support. The catalyst may be maintained in a fixed, moving or fluid bed. In general, this process is suited for treatment of the residua materials mentioned above and it is especially suited for treating residua containing at least 10 weight percent hydrocarbons having a boiling point greater than 900° F at atmospheric pressure. Furthermore, solid carbonaceous solid materials such as coke or coal may be added to the residua. Suitable alkali metal catalyst components include the carbonates, acetates, formates, sulfides, hydrosulfides, sulfites, vanadites, oxides and hydroxides of sodium, lithium, cesium and potassium. The solid particulate support may be chosen from a wide variety of materials including gasifiable solids, e.g. coal or activated carbon, and non-gasifiable solids such as zeolites or refractory inorganic oxides. A preferred catalyst comprises potassium or cesium carbonate mixed with or deposited on a refractory inorganic oxide such as alumina, silica, silica-alumina, magnesia, crude or partially refined bauxite or mixtures thereof. Typically, the process can be operated over a wide range of conditions as shown below.

| Range | Suitable | Preferred |
|---|---|---|
| Numerically Integrated Average Temperature, ° F | 1000–1500 | 1250–1450 |
| Pressure, psig | 200–1500 | 400–1000 |
| Alkali metal in Bed, wt. % | 1–35 | 4–24 |
| Space Velocity, weight part of feed per weight part of bed solids inventory per hour | 0.02–1 | 0.1–0.5 |
| Moles of steam/atoms of carbon in Feed | 0.7–15 | 1.7–5 |

Because the reaction of steam with carbon to produce a methane rich vaporous product under the above given conditions is an overall endothermic reaction, an oxygen-containing gas such as air or oxygen may be introduced into the reaction zone to provide at least a portion of the heat needed in said zone by the combustion of at least a portion of the feed and/or the carbonaceous material and/or gaseous products present therein.

Other gasification processes such as partial oxidation can be utilized as long as a synthesis gas containing from about 5–30 mole % methane as well as carbon monoxide and hydrogen is produced. It is preferred that the synthesis gas contain less than 5 mole % nitrogen. Examples of other gasification processes which can be used in the present invention are described in the following publications: U.S. Pat. Nos. 2,543,795; 2,609,283; 2,623,816; 2,634,198; 2,662,816; 2,687,950; 2,694,263; 2,694,624; 2,955,988; 3,194,644; 3,440,177 and 3,463,623. All of these publications are to be considered as incorporated herein by reference. In any of the gasification processes mentioned above, heat can be supplied to the gasification zone by a variety of methods additional to those mentioned with respect to the fluidized bed steam gasification zone above, including preheating the carbonaceous material, providing an electrical heating means within the gasification zone, utilizing heat from a nuclear reactor, and the like. Lurgi gasifiers may also be used in the present invention.

The synthesis gas thus formed is then introduced into a water gas shift conversion zone wherein at least a portion of the carbon monoxide present is converted catalytically, in the presence of steam, to carbon dioxide and hydrogen. Typically, the shift conversion zone contains at least one shift converter. The manner by which the conversion of carbon monoxide to carbon dioxide and hydrogen is controlled is not critical to the practice of the present invention and can be done in any one of a number of conventional methods that are well known to one skilled in the art, e.g. controlling the amount of steam present in the reaction zone, controlling the inlet or outlet temperatures of the reaction zone, removing or adding $CO_2$ prior to the shift conversion, by-passing a portion of the synthesis gas around the shift conversion zone, and the like. Any of these methods may be used to control the shift conversion reaction so as to satisfy the necessary stoichiometry for the subsequent production of methanol and additional quantities of methane. One method for adjusting the water content in the shift conversion zone is to use a hot water scrub of at least a portion of the synthesis gas at a controlled temperature.

The shift conversion zone will comprise either a so-called "high temperature" shift conversion zone or a "low temperature" shift conversion zone. The conventional use of both a high temperature and low temperature shift conversion zone in series is not required because a substantially carbon oxide-free hydrogen-containing gaseous product (such as that employed as $NH_3$ synthesis gas) is not desired for the practice of the present invention. The degree of carbon monoxide conversion should be such that the molar ratio of carbon monoxide to hydrogen in the converted synthesis gas ranges between 1:2 and 1:3 or 1:3.5, the particular ratio therein depending upon the amount of carbon dioxide allowed to pass to the subsequent methanol and methane steps and upon the amount of methanol and synthetic natural gas desired as product.

A conventional high temperature shift conversion zone is operated at elevated temperature and pressure and in the presence of a catalyst, said catalyst being any polyvalent metal or oxide thereof capable of converting carbon monoxide to carbon dioxide. Suitable catalysts include iron oxide, cobalt oxide, chromia, molybdena and tungsten oxide and the like. Other catalyst obvious to one skilled in the art may also be used. The inlet temperature of shift conversion employing the above catalysts will vary from about 600° F to 800° F. Because the shift conversion reaction is exothermic, the temperature of the gas during passage over the catalyst will rise beyond that of the inlet temperature so that the outlet temperature will vary from about 700° F. to about 1000° F. Typically, the pressure will range from about 50 to about 1500 psig, depending upon the pressure used for the gasification process. The space velocity during shift conversion at the above conditions may range from about 1000 to about 500 volumes of dry gas at standard conditions (60° F. and atmospheric pressure) per hour per volume of catalyst and preferably from about 2000 to about 3000.

Alternatively, the shift conversion can be effected in a conventional low temperature shift conversion zone wherein the inlet and outlet temperatures range from about 350° to about 600° F and from about 400° to about 650° F, respectively. The pressure employed during low temperature shift conversion will be substantially the same as high temperature shift conversion. The steam-dry gas ratio for both high or low temperature shift conversion will be from about 0.2 to 1 to about 1 to 1. However, lower or higher ratios of steam to dry gas may also be used depending on the specific design requirements of the manufacturing facility. The space velocity utilized for low temperature shift conversion depends upon the degree of carbon monoxide conversion desired and the steam-dry gas ratio employed. Generally, the space velocity may vary from about 2000 to about 4000, preferably from about 2500 to about 3500, volumes of dry gas at standard conditions (60° F and atmospheric pressure) per hour per volume of catalyst.

Other shift conversion processes such as, for example, that described in application Ser. No. 526,675, filed Nov. 25, 1974, which is a continuation-in-part of Ser. No. 235,178, filed Mar. 16, 1972, now abandoned, may also be employed. Application Ser. No. 526,675, the disclosures of which are incorporated herein by reference, discloses a shift conversion process operated at a temperature between about 200° and 950° F. in the presence of a catalyst comprising (1) an alkali metal compound derived from an acid having an ionization constant less than about $1 \times 10^{-3}$, (2) a hydrogenation-dehydrogenation component selected from the group consisting of (a) a non-noble metal composition comprising the oxides or sulfides of vanadium, molybdenum, tungsten, cobalt, tantalum or niobium or mixtures thereof or (b) mixtures of non-noble metal compounds comprising the oxides or sulfides of vanadium, molybdenum, tungsten, cobalt, tantalum or niobium or mixtures thereof with oxides or sulfides of nickel, iron or chromium or mixtures thereof, and (3) a halogen moiety. In this process, the pressure is maintained between atmospheric and 3000 psig and the weight ratio of the hydrogenation-dehydrogenation component to the alkali metal compound, each calculated on the basis of the oxide thereof, is less than 10:1. Water gas shift conversion catalysts may be in any suitable form such as granules, pellets, tablets and the like.

The converted synthesis gas is then passed to an acid gas removal zone wherein sulfur compounds, e.g. hydrogen sulfide, and carbon dioxide are removed therefrom. If desired, more than one chamber may be utilized to effect the desired amount of removal. Carbon dioxide can be removed from the converted synthesis gas by passing said gas through a vessel which contains a regenerative solvent capable of removing carbon dioxide. Among the solvents which may be used are monoethanolamine, diethanolamine, hot potassium carbonate and the like. An additive such as arsenic oxide diethanolamine may also be employed.

Hydrogen sulfide can be removed by the same regenerative solvents as well as by passing the converted synthesis gas, for example, through a solution such as ammonium thioarsenate. Organic sulfur compounds can also be removed from the synthesis gas by passing said gas over hot lime or activated aluminum oxide which converts said compounds to hydrogen sulfide. The hydrogen sulfide thus formed can then be removed by passing the gas through a caustic scrubber wherein all traces of carbon dioxide are also removed. It is to be understood that the foregoing processes for the removal of sulfur compounds and substantially all of the carbon dioxide are exemplary only and other processes can be utilized as long as the desired end results are achieved. However, the complete removal of carbon dioxide is not essential since it also reacts with hydrogen, just as carbon monoxide, to form methanol and methane in subsequent conversion zones.

The purified and converted synthesis gas is then introduced into a methanol synthesis zone. The composition of said synthesis gas, prior to the conversion of a portion of said synthesis gas in the methanol synthesis zone, will vary depending upon the type of carbonaceous solid or liquid material processed in the gasification zone and the amount of methane and methanol product desired.

The synthesis of methanol may be represented in a simplified manner by the three basic overall reactions which follow:

(a) $CO + 2H_2 \longrightarrow CH_3OH$
(b) $CO_2 + 3H_2 \longrightarrow CH_3OH + H_2O$
(c) $CO_2 + H_2 \longrightarrow CO + H_2O$ These reactions, as well as other minor reactions which also take place in the methanol reaction zone or methanol converter, occur at elevated temperature and pressure and in the presence of a catalyst. The temperature for methanol synthesis may vary from about 400° F to about 700° F, preferably from about 425° F to about 575° F. Temperatures in excess of 600° F may be used with caution where one so desires as long as the desired result is obtained. However, at temperatures greater than 600° F, there is danger of excessive methane formation and temperature runaways. The pressure for methanol synthesis may vary from about 400 to about 1500 psig.

The catalyst used for the methanol synthesis may be either a single catalyst or a mixture of catalysts. It may be finely ground, pelleted, granular in nature, an extrusion using a binding agent, or in any other suitable form. Among the catalysts which may be used are partially reduced oxides of copper, zinc and chromium, zinc oxide and chromium oxide, zinc oxide and copper, copper and aluminum oxide or cerium oxide, zinc oxide and ferric hydroxide, zinc oxide and cupric oxide, a copper zinc alloy, and oxides of zinc, magnesium, cadmium, chromium, vanadium and/or tungsten with oxides of copper, silver, iron and/or cobalt, and the like. The invention is not to be construed as limited to any particular catalyst or catalyst system as other catalysts which are well known in the art may also be used.

The methanol synthesis zone is typically a pressure vessel containing a charge of catalyst arranged in the vessel as a continuous bed or, alternatively, as several independently supported catalyst beds. Facilities are provided in the converter to permit heat removal, or, alternatively, for the injection of cold synthesis gas directly into the catalyst bed or between the catalyst beds to control the reaction temperature. The quantity of catalyst provided in the converter will depend on the pressure employed during methanol synthesis, the composition of synthesis gas, and the degree of conversion of synthesis gas to methanol in each catalyst bed. The space velocity employed in the methanol synthesis converter will vary from about 5000 to about 50,000, preferably from about 7000 to about 25,000 volumes of dry gas at standard conditions (60° F and atmospheric pressure) per hour per volume of catalyst.

If desired, prior to recovering the methanol product, the effluent from the methanol converter is heat exchanged with a portion of the incoming synthesis gas to preheat said gas to a temperature sufficient to initiate the methanol synthesis reaction. The methanol converter effluent may then be water cooled to condense the methanol and any water formed in the methanol synthesis zone. The amount of water contained in the methanol thus synthesized will depend upon the amount of carbon dioxide remaining in the gas discharged from the acid gas removal zone which is subsequently reacted in the methanol synthesis zone and the amount of water present in the methanol synthesis gas feed.

Any suitable system may be used to purify the methanol thus synthesized. One such system comprises a topping column operating at low pressure, e.g. up to about 20 psig, which contains a plurality of bubble trays designed to remove light components contained in the methanol. The number of bubble trays employed will vary depending upon the desired purity of the methanol product, the pressure used in the column, the amount of heat supplied to the column and other factors. The partially refined methanol from the topping column may then be sent to a refining column. This column operates at low pressure, e.g. about 30 psig, and serves to separate methanol from water and high boiling organic compounds. The number of bubble trays employed in the refining column will also vary according to the desired quality of the methanol product.

The degree of purity required for the methanol product depends on the final product disposition. If the methanol is to be used merely as a fuel, very little, if any, purification may be required. However, it may be desirable to stabilize the product to eliminate highly volatile dimethyl ether, but a rerunning operation to remove water via fractionation is usually not required when using the process of the present invention. This is one of the advantages of the present combination in that the acid gas scrubbing eliminates the bulk of the carbon dioxide in the methanol feed gas. Since it is carbon dioxide which forms water in the methanol synthesis reaction zone according to equation (b) shown above, very little water is formed therein. Consequently, the product may be a satisfactory fuel without the expensive and heat-consuming methanol/water distillation.

In conventional methanol plants, the carbon dioxide content of the synthesis gas from steam reforming is always high enough to yield 10–20 wt. % water on methanol in the converter. Acid gas removal is not required and thus not done in conventional methanol plants. However, it is required in synthetic natural gas plants to make a high Btu product. This is another advantage of the present combination wherein a process step and a product requirement favorably influence the production of the other.

The synthesis gas which exits the methanol synthesis reaction zone contains hydrogen, carbon monoxide, methane and a small amount of carbon dioxide. This gas then undergoes methanation to convert the remaining carbon oxides to methane. The methanation process comprises various chambers which are connected to one another via a suitable arrangement of pipes and valves. This conversion involves the reaction of carbon monoxide and carbon dioxide with hydrogen in a molar ratio of about 1:3 or 1:4, respectively. The temperatures for such conversion will vary, but, in general, will range from about 400° to about 800° F. The inlet temperature in the methanation chamber will vary, for example, from about 400° to about 600° F. and the outlet temperature from about 600° to about 750° F. The pressure at which methanation is effected will range from about 250 to about 1500 psig, preferably from about 300 to about 1000 psig. The catalyst which is used to effect the methanation may be a partialy reduced nickel oxide catalyst or any other suitable catalyst known in the art. Thus the invention is not to be construed as limited to any particular methanation catalyst or any particular temperatures and pressures.

By using the present invention, the ratio of the rate of methanol production to synthetic natural gas production may be varied to produce more methanol and less synthetic natural gas or vice versa. It is even possible to product methanol or synthetic natural gas beyond the rated capacity of the methanol or synthetic natural gas facilities by eliminating or reducing the production of methanol or by minimizine the production of synthetic natural gas.

Such versatility enables the integrated process of the present invention to respond to changes in economic factors. For example, during periods of peak gas demand, it may be desirable to curtail methanol production. This is easily done by passing the gas from the acid gas removal zone to the methanation zone rather than the methanol synthesis zone. Conversely, during periods of low gas demand, conversion to methanol can be maximized without decreasing the synthesis gas generation portion of the plant by recycling gas from the methanol synthesis to the methanol converters or by providing additional methanol reactor/condensing stages.

In line with the above flexibility, methanol synthesis can be considered as a fly-wheel that permits steady operation in the synthetic natural gas synthesis portion of the present invention, independent of the gas demand. If so desired, conversion of stored methanol product to gas during periods of exceedingly high gas demand can be considered an another advantage of the present combination. Additionally, because of the integration of processes in the present invention, costly equipment, such as duplicate steam generating facilities, a carbon dioxide compressor, methanol synthesis loop or recycle, and associated equipment which normally would have to be included in separate manufacturing facilities are eliminated.

Utilizing the process conditions set forth in Tables I and II for bituminous coal in application Ser. No. 509,880 and with reference to the FIGURE and process conditions of the present invention, the following is a typical analysis of the gas at each step of the present invention:

TABLE I

| Component, in 1000 mols/hr. | Gasifier Effluent | Shift Effluent | $CO_2$ Removal Effluent | Methanol Conversion Product | Methanation Product |
|---|---|---|---|---|---|
| $H_2$ | 26.9 | 31.3 | 31.1 | 20.6 | 1.1 |
| CO | 14.7 | 10.5 | 10.5 | 5.4 | Trace |
| $CO_2$ | 11.8 | 16.0 | 1.4 | 1.2 | 0.4 |
| $CH_4$ | 15.8 | 15.8 | 15.8 | 15.8 | 22.0 |
| $H_2S$ | 1.3 | 1.3 | — | — | — |
| $H_2O$ | 28.5 | 2.9 | 3.3 | 0.1 | — |
| $CH_3OH$ | — | — | — | 5.2 | — |
| Other | 1.0 | 0.8 | 0.8 | 0.4 | 0.4 |
| Total | 100.0 | 78.4 | 62.9 | 48.7 | 23.9 |

Reference to Table I shows that the amount of methanol produced (5,200 mols/hr) represents about 20% of the total carbon value from the gasification zone (22,000 mols/hr of methane plus 5,200 mols/hr of methanol). The amount of $CO_2$ which has to be removed in the $CO_2$ scrubber is 14,600 mols/hr, and the shift converter duty is 4,200 mols/hr of CO shifted to $H_2$ and $CO_2$.

If methanol were not co-produced, 5,900 mols/hr of CO would have to be shifted such that the $CO_2$ scrubber duty woild have to be increased to 16,300 mols/hr to achieve the molar ratio of carbon monoxide to hydrogen of 1:3 required for the methanation reaction. Therefore, as a result of the present combination process, the duties of both the shift converter and the $CO_2$ scrubber are decreased relative to those required when methane is the only product.

The decrease in methane production between that produced by only a synthetic natural gas plant and that produced by the combination process of the present invention is about 3,600 mols/hr. If the 5,200 mols/hr of methanol produced by the combination process were utilized as fuel, there will be a considerable increase (approximately 15%) in fuel value of the incremental product.

A further improvement in the synthetic natural gas synthesis due to the co-production of methanol is found in the methanation section. As is apparent from Table I, in the present combination process, the methanator must convert 6,200 mols/hr of carbon oxides (mostly CO) into methane in the presence of about 16,000 mols/hr of methane which will act as a heat sink during the highly exothermic methanation reaction. On the other hand, when there is no coproduction of methanol, the 16,000 mols/hr of methane will act as heat sink for the methanation of 9,800 mols/hr of carbon oxides (again mostly CO), a much more severe heat load. Consequently, co-production of methanol will have a favorable affect on the design of the methanation section of the present invention. Thus, the co-production of methanol results in major improvements in the shift conversion, acid gas scrubbing and methanation sections of the synthetic natural gas plant. In addition, as noted above, the co-production of a gas and liquid fuel provides flexibility in the overall plant operation and therefore simplifies the design of all sections so as to meet fluctuating demands of the gas product.

The methanol synthesis section of the combination process also has distinct advantages relative to a facility producing only methanol. As noted above, one advantage is in minimizing the water produced in the methanol reactor and the resultant simplification in product purification equipment. Another advantage is the elimination of the recycle compressor since a high conversion of the carbon oxides and hydrogen to methanol is not required. Any CO, $CO_2$ and $H_2$ not converted during methanol synthesis is passed to the methanator and converted therein to methane. Although a portion of the gas from the methanol synthesis can be recycled to the methanol reactor, a once-through operation has the advantage of being able to tolerate a higher level of inerts (specifically methane, ethane and nitrogen) in the feed gas, i.e. the gas feed to the methanol synthesis. In a conventional methanol plant with recycle, the inerts accumulate rapidly and quickly choke the reaction unless a high, and uneconomical, purge rate is imposed.

A further advantage in the methanol synthesis employed in the present combination process relative to a facility producing only methanol is the required selectivity of the catalyst to methanol versus methane formation. In a methanol-only plant, methane formation is highly undesirable since it rapidly accumulates as an inert in the recycle gas, thereby requiring the uneconomically high purge rates mentioned above. Thus, valuable feed gas is lost not only by conversion to methane, but also in the excess purge which must be removed from the recycle loop to maintain the level of inerts in the reactor at an acceptable level. In contrast to this, a modest amount of methane made in the methanol reactors, coupled with adequate heat removal for the high heat of reaction of methanation, is not undesirable in the present combination process and may actually be helpful. The amount of carbon monoxide converted to methane during methanol synthesis only reduces the amount that need be converted in the methanator. Since most methanol catalysts exhibit increasing methanation activity with increasing temperature and catalyst age, the production of up to 20%, on a molar basis, of methane compared to methanol in the methanol reactor allows longer catalyst life and a wider temperature range than a conventional operation.

The activity of methanol catalysts toward methanation at increased temperature can be used advantageously in the operation of this combination plant during high gas demand periods. By increasing the temperature in the methanol reactors from 400°–600° F. to 700°–800° F, the reactors can be used as pre-methanators to take some of the methanation load off the subsequent methanation zone.

Thus, the integrated process of the present invention provides for the concurrent production of methanol and synthetic natural gas at a cost substantially less than two separate process facilities.

While the present invention described above includes a shift conversion zone, if the molar ratio of carbon monoxide to hydrogen in the synthesis gas from the gasification zone is at least 1:2.3 and preferably is in the range from 1:2.3 to about 1:3, the synthesis gas can be passed directly to the acid gas removal zone. If done in this manner, the ratio of carbon oxides subsequently converted to methanol and methane may be varied by controlling the amount of carbon dioxide removed in the acid gas removal zone. As more carbon dioxide is removed therefrom, the molar ratio of carbon oxides to hydrogen is decreased which corresponds to the stoichiometry of increased methane production.

What is claimed is:

1. An integrated process for the production of methanol and a synthetic natural gas, which is substantially methane, from a carbonaceous material which comprises the steps of:
   a. Gasifying the carbonaceous material in a first reaction zone at sufficient pressure and temperature to produce a synthesis gas stream comprising methane, carbon monoxide, carbon dioxide, hydrogen, and steam, in which the synthesis gas contains about 5°–30 mole % methane on a dry basis;
   b. Passing said synthesis gas stream to a second reaction zone wherein at least a portion of said carbon monoxide is reacted with at least a portion of the steam present therein and is converted at a sufficient temperature and pressure and in the presence of a water gas shift conversion catalyst, to carbon dioxide and hydrogen, thereby producing a converted gas stream with the proviso that the shift conversion is controlled to such an extent as to provide the necessary stoichiometry for the subsequent production of methanol and additional quantities of methane;
   c. Passing said converted stream to a third zone wherein the sulfur compounds and a major portion of the carbon dioxide in said converted stream are removed therefrom to produce a purified stream;
   d. Passing said purified stream into a fourth reaction zone wherein a portion of the carbon oxides and hydrogen in said purified stream are converted, in the presence of a methanol conversion catalyst and at a sufficient temperature and at pressures ranging from 400 to about 1500 psig, to methanol;
   e. Recovering methanol from said fourth reaction zone and separately recovering the unreacted portion of said purified stream which contains a reduced amount of carbon oxides;
   f. Passing the unreacted portion of said purified stream containing the remaining carbon oxides, hydrogen, and the methane produced in the first reaction zone from said fourth reaction zone to a fifth reaction zone wherein said remaining carbon oxides and hydrogen are converted, in the presence of a methanation catalyst and at a sufficient temperature and pressure, to methane.

2. The process of claim 1 wherein the conditions within said second reaction zone comprise a temperature between about 200° F. and 950° F. and a pressure between about 15 psia and 3000 psia.

3. The process of claim 1 wherein the conditions within said fifth reaction zone comprise a temperature between about 400° F. and 800° F. and a pressure between about 250 psig and 1500 psig.

4. The process of claim 3 wherein said fourth reaction zone comprises at least two methanol converters in series, each converter having a methanol removal means thereafter in series.

5. The process of claim 1 wherein the carbonaceous material is atmospheric residuum, vacuum residuum, or mixtures thereof.

6. The process of claim 1 wherein the carbonaceous material is coke.

7. The process of claim 1 wherein the carbonaceous material is cellulosic material.

8. The process of claim 1 wherein the carbonaceous material is municipal waste.

9. The process of claim 1 wherein the gasification in the first reaction zone is a partial oxidation of said carbonaceous material.

10. The process of claim 1 wherein the gasification in the first reaction zone is the gasification of said carbonaceous material in the presence of steam, an oxygen-containing gas and a particulate catalyst containing an alkali metal component, a solid support and an in situ formed carbonaceous deposit on said support.

11. The process of claim 1 wherein the reaction conditions in said fourth reaction zone are such as to provide that not more than approximately one-fifth of the carbon oxides reacted are converted to methane and approximately four-fifths of said carbon oxides are converted to methanol.

12. The process of claim 1 wherein the molar ratio of carbon monoxide to hydrogen in the synthesis gas discharged from the gasification zone is at least 1:2.3 and said gas is passed directly to the acid gas removal zone.

13. An integrated process for the production of methanol and a synthetic natural gas, which is substantially methane, from a carbonaceous material selected from the group consisting of coal, residua or mixtures thereof which comprises the steps of:
 a. Gasifying the carbonaceous materials in a first reaction zone at sufficient pressure and temperature to produce a synthesis gas stream comprising methane, carbon monoxide, carbon dioxide, hydrogen, and steam, in which the synthesis gas contains about 10–30 mole % methane on a dry basis;
 b. Passing said synthesis gas stream to a second reaction zone wherein at least a portion of said carbon monoxide is reacted with at least a portion of the steam present therein and is converted, at a sufficient temperature and pressure and in the presence of a water gas shift conversion catalyst, to carbon dioxide and hydrogen, thereby producing a converted gas stream with the proviso that the shift conversion is controlled to such an extent as to provide the necessary stoichiometry for the subsequent production of methanol and additional quantities of methane;
 c. Passing said converted stream to a third zone wherein the sulfur compounds and substantially all carbon dioxide in said converted stream are removed therefrom to produce a purified stream;
 d. Passing said purified stream into a fourth reaction zone wherein a portion of the carbon oxides and hydrogen in said purified stream are converted, in a once-through process, in the presence of a methanol conversion catalyst and at a sufficient temperature and at pressures ranging from 400 to about 1500 psig, to methanol;
 e. Recovering methanol from said fourth reaction zone and separately recovering the unreacted portion of said purified stream which contains a reduced amount of carbon oxides;
 f. Passing the unreacted portion of said purified stream containing the remaining carbon monoxide, hydrogen and methane produced in the first reaction zone from said fourth reaction zone to a fifth reaction zone wherein said remaining carbon oxides and hydrogen are converted, in the presence of a methanation catalyst and at a sufficient temperature and pressure, to methane.

14. The process of claim 1 wherein the carbonaceous material is selected from the group consisting of coal, residua and mixtures thereof.

15. The process of claim 1 wherein the carbonaceous material is coal.

16. The process of claim 2, wherein the first reaction zone comprises two sections, the first section wherein steam and char are reacted together to provide a synthesis gas and heated solids, and the second section wherein coal is cocurrently passed with the synthesis gas and heated solids through said second section which is a transfer line hydrogasification zone.

17. The process of claim 13 wherein the carbonaceous material is coal.

18. The process of claim 17 wherein the first reaction zone comprises two sections, the first section wherein steam and char are reacted together to provide a synthesis gas and heated solids, and the second section wherein coal is cocurrently passed with the synthesis gas and heated solids through said second section which is a transfer line hydrogasification zone.

19. The process of claim 13 wherein said fourth reaction zone comprises at least two methanol converters in a series, each converter having a methanol removal means thereafter in series.

20. The process of claim 13 wherein the gasification in the first reaction zone is the gasification of said carbonaceous material in the presence of steam, an oxygen-containing gas and a particulate catalyst containing an alkali metal component, a solid support and an in situ formed carbonaceous deposit on said support.

21. The process of claim 13 wherein the molar ratio of said carbon monoxide to hydrogen in a synthesis gas discharged from the gasification zone is at least 1:2.3 and said gas is passed directly to the acid gas removal zone.

* * * * *